US00PP35991P2

(12) United States Plant Patent
van Sambeek

(10) Patent No.: US PP35,991 P2
(45) Date of Patent: Jul. 9, 2024

(54) ***IBERIS* PLANT NAMED 'DOIBEXWHI'**

(50) Latin Name: *Iberis sempervirens*
Varietal Denomination: Doibexwhi

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/382,503

(22) Filed: Oct. 21, 2023

(51) Int. Cl.
*A01H 5/02* (2018.01)
*A01H 6/20* (2018.01)

(52) U.S. Cl.
USPC ..... Plt./263.1
CPC ..... *A01H 6/20* (2018.05)

(58) Field of Classification Search
USPC ..... Plt./263.1
CPC ..... A01H 6/20; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Iberis* plant named 'Doibexwhi', characterized by its compact, upright to outwardly spreading and uniformly mounding plant habit; moderately vigorous growth habit; freely branching habit; dense and bushy habit; relatively late flowering; numerous dense inflorescences with light purple-colored flowers; and good container and garden performance.

1 Drawing Sheet

Botanical designation: *Iberis sempervirens*.
Cultivar denomination: 'DOIBEXWHI'.

STATEMENT REGARDING PRIOR DISCLOSURES BY INVENTOR & APPLICANT/ASSIGNEE

An European Community Plant Breeder's Rights application for the instant plant was filed by the Inventor/Applicant on Aug. 22, 2022, application number 2022/1994. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or the Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Iberis* plant, botanically known as *Iberis sempervirens* and hereinafter referred to by the name 'Doibexwhi'.

The new *Iberis* plant is a product of a planned breeding program conducted by the Inventor in Aalsmeer, The Netherlands. The objective of the breeding program is to create new freely branching *Iberis* plants with large flowers and large inflorescences.

The new *Iberis* plant originated from a cross-pollination conducted by the Inventor in April, 2017 in Aalsmeer, The Netherlands of *Iberis sempervirens* 'Pink Ice', disclosed in U.S. Plant Pat. No. 23,854, as the female, or seed parent with a proprietary selection of *Iberis sempervirens* identified as code number IB-0004, not patented, as the male, or pollen, parent. The new *Iberis* plant was discovered and selected by the Inventor as a single flowering plant from within the progeny of the stated open-pollination in a controlled greenhouse environment in Aalsmeer, The Netherlands in April, 2018.

Asexual reproduction of the new *Iberis* plant by vegetative terminal cuttings in a controlled greenhouse environment in since June, 2018 has shown that the unique features of this new *Iberis* plant are stable and reproduced true to type in successive generations.

SUMMARY OF THE INVENTION

Plants of the new *Iberis* have not been observed under all possible combination of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doibexwhi'. These characteristics in combination distinguish 'Doibexwhi' as a new and distinct *Iberis* plant:

1. Compact, upright to outwardly spreading and uniformly mounding plant habit.
2. Moderately vigorous growth habit.
3. Freely branching habit; dense and bushy habit.
4. Relatively late flowering.
5. Numerous dense inflorescences with light purple-colored flowers.
6. Good container and garden performance.

Plants of the new *Iberis* differ primarily from plants of the female parent, 'Pink Ice', in the following characteristics:

1. Plants of the new *Iberis* are more compact than plants of 'Pink Ice'.

2. Leaves of plants of the new *Iberis* are darker green in color than leaves of plants of 'Pink Ice'.

Plants of the new *Iberis* differ primarily from plants of the male parent selection in the following characteristics:

1. Plants of the new *Iberis* flower later than plants of the male parent selection.
2. Flowers of plants of the new *Iberis* are light purple in color whereas flowers of plants of the male parent selection are white in color.

Plants of the new *Iberis* can be compared to plants of *Iberis hybrida* 'IB2401', disclosed in U.S. Plant Pat. No. 23,048. In side-by-side comparisons, plants of the new *Iberis* differ from plants of 'IB2401' in the following characteristics:

1. Plants of the new *Iberis* are more outwardly spreading than and not as upright as plants of 'IB2401'.
2. Plants of the new *Iberis* have smaller leaves than plants of 'IB2401'.
3. Flowers of plants of the new *Iberis* are light purple in color whereas flowers of plants of 'IB2401' are dark violet in color.

BRIEF DESCRIPTION OF THE PHOTOGRAPH

The accompanying photograph illustrates the overall appearance of the new *Iberis* plant showing the colors as true as it is reasonably possible to obtain in colored reproductions of this type. Colors in the photograph may differ slightly from the color values cited in the detailed botanical description which accurately describe the colors of the new *Iberis* plant. The photograph is a side perspective view of a typical flowering plant of 'Doibexwhi' grown in a container.

DETAILED BOTANICAL DESCRIPTION

The aforementioned photograph and following observations and measurements describe plants grown during the spring in 17-cm containers initially in a glass-covered greenhouse and finished in an outdoor nursery in Aalsmeer, The Netherlands and under cultural practices typical of commercial *Iberis* production. During the production of the plants, average daily temperatures were 21 C and average night temperatures were 15 C. Plants were pinched two weeks after planting and were 49 weeks old when the photograph and description were taken. In the following description, color references are made to The Royal Horticultural Society Colour Chart, Fifth Edition, except where general terms of ordinary dictionary significance are used.

Botanical classification: *Iberis sempervirens* 'Doibexwhi'.

Parentage:

*Female, or seed, parent.*—*Iberis sempervirens* 'Pink Ice', disclosed in U.S. Plant Pat. No. 23,854.

*Male, or pollen, parent.*—Proprietary selection of *Iberis sempervirens* identified as code number IB-0004, not patented.

Propagation:

*Type.*—Terminal vegetative cuttings.

*Time to initiate roots, summer.*—About 16 days at temperatures about 26 C.

*Time to initiate roots, winter.*—About three weeks at temperatures about 23 C.

*Time to produce a rooted cutting, summer.*—About 24 days at temperatures about 23 C.

*Time to produce a rooted cutting, winter.*—About four weeks at temperatures about 5 C.

*Root description.*—Medium in thickness, fibrous; typically white to light yellow in color, actual color of the roots is dependent on substrate composition, water quality, fertilizer type and formulation, substrate temperature and physiological age of roots.

*Rooting habit.*—Moderately freely branching habit; medium density.

Plant description:

*Plant and growth habit.*—Perennial, good performance as a container and garden plant; compact, upright to outwardly spreading and uniformly mounding plant habit; moderately vigorous growth habit and moderate growth rate; freely branching habit; about four primary branches develop per plant each with about 60 secondary laterals; dense and bushy habit; pinching enhances lateral branch development.

*Plant height.*—About 22 cm.

*Plant diameter.*—About 38 cm.

Lateral branch description:

*Length.*—About 18 cm.

*Diameter.*—About 2 mm.

*Internode length.*—About 6 mm.

*Strength.*—Strong.

*Aspect.*—Upright to about 45 degrees from vertical.

*Texture and luster.*—Smooth, glabrous; glossy.

*Color, developing and developed.*—Close to 143B.

Leaf description:

*Arrangement.*—Alternate, simple; sessile.

*Length.*—About 1.3 cm.

*Width.*—About 5 mm.

*Shape.*—Linear.

*Apex.*—Acute.

*Base.*—Cuneate.

*Margin.*—Mostly entire; occasionally one or two shallow indentations.

*Texture and luster, upper and lower surfaces.*—Smooth, glabrous; glossy.

*Venation pattern.*—Single midvein discernible.

*Color.*—Developing leaves, upper and lower surfaces: Close to 139A. Fully expanded leaves, upper and lower surfaces: Close to 139A; venation, close to 139A.

Flower description:

*Flower arrangement and habit.*—Cruciferous flowers arranged in terminal corymbs; flowers face mostly upright; freely flowering habit with about 35 flowers per inflorescence with about 15,900 flowers developing during the flowering season.

*Fragrance.*—Faintly fragrant; pleasant.

*Natural flowering season.*—Plants flower about 49 weeks after planting and flower naturally in May and June in The Netherlands; flowering period lasts about three to four weeks; flowers persistent.

*Inflorescence height.*—About 2.1 cm.

*Inflorescence diameter.*—About 3.5 cm.

*Flower buds.*—Length: About 3 mm. Diameter: About 3 mm. Shape: Ovoid. Texture and luster: Smooth, glabrous; matte. Color: Close to 155D and 76B.

*Flower diameter.*—About 3 mm by 14 mm.

*Flower depth.*—About 1.2 cm.

*Petals.*—Arrangement: Four petals in a single whorl; two smaller and two larger petals. Length: Smaller petals: About 1 mm. Larger petals: About 1 cm. Width: Smaller petals: About 3 mm. Larger petals: About 7 mm. Shape, all petals: Obovate. Apex, all petals: Obtuse. Base, all petals: Obtuse. Margin, all petals: Entire; not undulate. Texture and luster, all petals, upper and lower surfaces: Smooth, glabrous; matte. Color, all petals: When opening, upper and lower surfaces: Close to 76A. Fully opened, upper and lower surfaces: Close to 76B; color becoming closer to NN155D with subsequent development.

*Sepals*.—Arrangement: Calyx with four sepals in a single whorl. Calyx length: About 4 mm. Calyx diameter: About 6 mm. Length: About 4 mm. Width: About 2 mm. Shape: Elliptic. Apex: Acute. Base: Obtuse. Margin: Entire. Texture and luster, upper and lower surfaces: Smooth, glabrous; glossy. Color, upper and lower surfaces: Close to 143A tinged with close to 70A.

*Peduncles*.—Length: About 3.5 cm. Diameter: About 3 mm. Angle: About 45 degrees from lateral branch axis. Strength: Moderately strong. Texture and luster: Smooth, glabrous; glossy. Color: Close to 143A.

*Pedicels*.—Length: About 5 mm. Diameter: About 1 mm. Angle: Erect to about 45 degrees from peduncle axis depending on position on corymb. Strength: Low, flexible. Texture and luster: Smooth, glabrous; glossy. Color: Close to 143C.

*Reproductive organs*.—Stamens: Quantity: Six per flower. Filament length: About 3 mm. Filament color: Close to N87B tinged with close to 143C. Anther shape: Elliptic. Anther size: About 0.5 mm by 0.5 mm. Anther color: Close to 6A. Pollen amount: Abundant. Pollen color: Close to 6A. Pistils: Quantity: One per flower. Pistil length: About 5 mm. Style length: About 2 mm. Style color: Close to N79A. Stigma diameter: About 1 mm. Stigma shape: Rounded, capitate. Stigma color: Close to 143C. Ovary color: Close to 143C tinged with close to N79A.

*Seeds and fruits*.—To date, seed and fruit development have not been observed on plants of the new *Iberis*.

Pathogen & pest resistance: To date, plants of the new *Iberis* have not been observed to be resistant to pathogens and pests common to *Iberis* plants.

Garden performance: Plants of the new *Iberis* have been observed to have good garden performance and to tolerate wind, rain, temperatures ranging from about −20 C to about 35 C and to be suitable for USDA Hardiness Zones 5 through 9.

It is claimed:

1. A new and distinct *Iberis* plant named 'Doibexwhi' as illustrated and described.

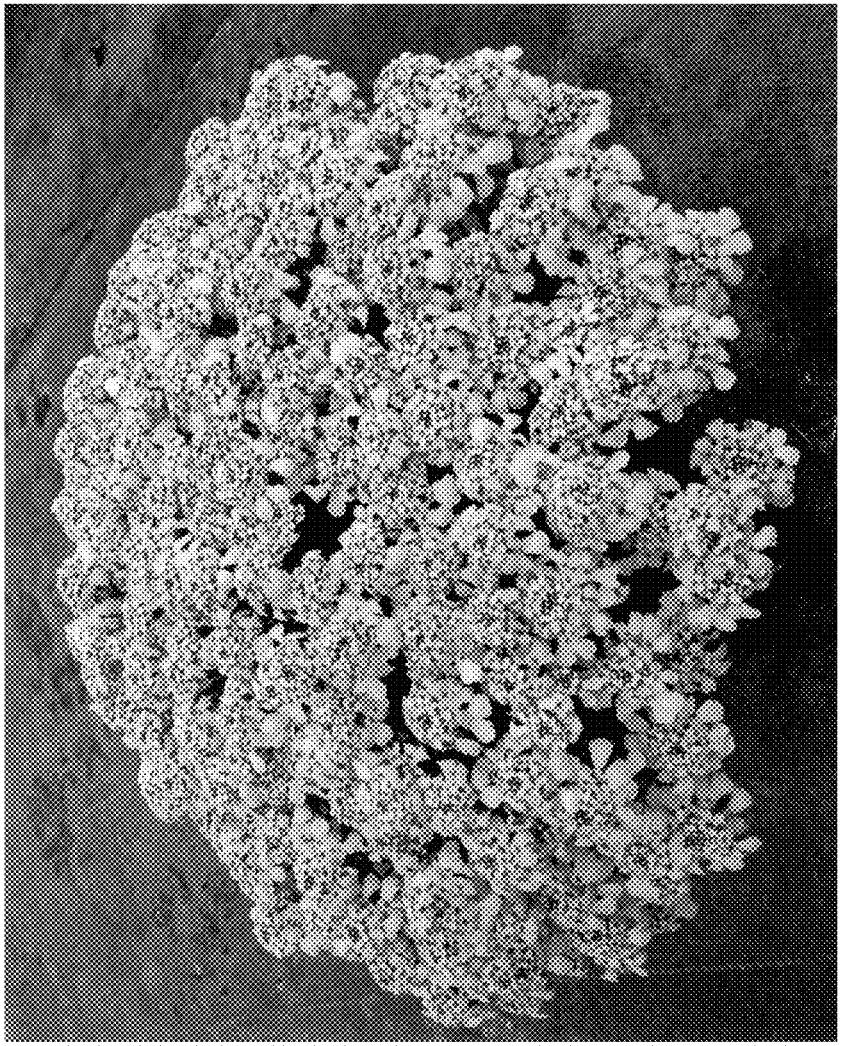

* * * * *